(12) United States Patent
Kim et al.

(10) Patent No.: US 8,382,823 B2
(45) Date of Patent: Feb. 26, 2013

(54) BIODEGRADABLE STENT AND METHOD FOR MANUFACTURING THE SAME

(75) Inventors: Hyoun Ee Kim, Seoul (KR); Ji Hoon Jo, Anyang-si (KR); Sang Beom Kim, Daejeon (KR)

(73) Assignee: SNU R&DB Foundation, Seoul (KR)

( * ) Notice: Subject to any disclaimer, the term of this patent is extended or adjusted under 35 U.S.C. 154(b) by 314 days.

(21) Appl. No.: 12/765,715

(22) Filed: Apr. 22, 2010

(65) Prior Publication Data

US 2010/0305684 A1 Dec. 2, 2010

(30) Foreign Application Priority Data

May 28, 2009 (KR) ........................ 10-2009-0046869

(51) Int. Cl.
*A61F 2/86* (2006.01)
(52) U.S. Cl. ...................................... 623/1.44
(58) Field of Classification Search .................. 623/1.44
See application file for complete search history.

(56) References Cited

U.S. PATENT DOCUMENTS

2008/0071358 A1*  3/2008  Weber et al. ................. 623/1.42
2009/0030506 A1*  1/2009  Klocke et al. ................ 623/1.46

OTHER PUBLICATIONS

Dieringa, "Mechanical and Corrosion Behaviour of a Hydroxyapatite Reinforced Magnesium Alloy WE43", GKSS Research, Centre, pp. 1-7, date accessed Apr. 18, 2012.*

* cited by examiner

*Primary Examiner* — Thomas J Sweet
*Assistant Examiner* — Rebecca Preston
(74) *Attorney, Agent, or Firm* — Seed IP Law Group PLLC

(57) ABSTRACT

A stent includes a magnesium layer, a ceramic layer formed over the magnesium layer, and a magnesium compound layer interposed between the magnesium layer and the ceramic layer. The initial corrosion of the stent can be delayed, and the stent has excellent biocompatibility and thus can reduce side effects during cell proliferation and differentiation.

18 Claims, 15 Drawing Sheets

(a)            (b)

(a)            (b)

(a) Pure Mg (b) MgF$_2$ coating (c) HA/MgF$_2$ coating

BIODEGRADABLE STENT AND METHOD FOR MANUFACTURING THE SAME

CROSS-REFERENCE TO RELATED APPLICATION

This application claims priority to and the benefit of Korean Patent Application No. 10-2009-0046869, filed May 28, 2009, the disclosure of which is incorporated herein by reference in its entirety.

BACKGROUND

1. Field

The present disclosure relates to a biodegradable stent and a manufacturing method thereof.

2. Discussion of Related Technology

Biodegradable materials which can be naturally degraded and absorbed in vivo are attracting attention as a new paradigm for biomaterials. The use of biodegradable materials makes it possible to solve problems caused by permanent biomaterials, including stress shielding, accumulation of toxic metal ions, and secondary surgery for removal of inserted materials.

Particularly, synthetic biodegradable polymers such as polylactic acid (PLA), polyglycolic acid (PGA) and polycaprolactone (PCL) have been widely used as a substitute for permanent biomaterials in orthopedic surgical applications. However, despite excellent biocompatibility, biodegradable polymers are limited in use due to low mechanical strength, the possible release of toxic substances after degradation, and a low degradation rate.

Recently, magnesium (Mg) and its alloys have attracted attention as promising biodegradable materials, because they provide excellent advantages, particularly excellent mechanical properties, compared to synthetic biodegradable polymers. Magnesium has an elastic modulus and compressive yield strength similar to those of natural bone and has a fracture toughness greater than that of natural bone. Thus, magnesium and its alloys have a great potential for load-bearing applications. Furthermore, magnesium has excellent biocompatibility, and released magnesium ions are beneficial for the growth of bone tissue, rather than harmful to the human body.

Nevertheless, the use of magnesium in biomedical applications is limited because of its high corrosion rate in an in vivo environment. Magnesium in aqueous solution reacts rapidly to produce byproducts such as $Mg^{2+}$ ion, hydroxide and hydrogen gas, which may be harmful to the surrounding tissues. This phenomenon is accelerated in chlorine-containing solutions such as body fluid. Because magnesium is degraded very rapidly, it can weaken the stability of biomaterials in vivo and reduce the biocompatibility of magnesium biomaterials. Thus, it is required to guarantee the initial stability of magnesium biomaterials by improving the corrosion resistance of magnesium.

Numerous methods for improving the corrosion resistance of magnesium to allow it to be used in bone implants have been studied, and examples thereof include alloying, mechanical processing and surface modification.

Specifically, magnesium alloys containing zinc (Zn) and manganese (Mn) show much higher corrosion resistance in Hank's solution (Hank's balance salt solution (HBSS)) than does pure magnesium, and binary Mg—Ca alloys have not only significant biocompatibility, but also mechanical and corrosion properties which can be adjusted depending on the calcium content.

Mechanical processing can be used to control the biodegradability of magnesium. For example, by performing hot rolling, the corrosion rate of magnesium alloy AZ31 can be reduced.

Particularly, surface modification of biomaterials is a suitable method for improving all biocompatibility and corrosion properties. It has indeed been used in metal implants such as stainless steel, titanium and its alloys. Because the surface of biomaterials reacts directly with body fluid in vivo and interacts with the surrounding tissues, the surface properties of biomaterials are critical for the performance of the biomaterials. Various surface treatments, including anodizing, electrodeposition, phosphating treatment, ion plating and fluoride conversion coating, have been used to improve the corrosion properties of the magnesium surface.

The results of electrochemical and immersion tests shows that the biodegradation rate of magnesium in chlorine-containing solutions is significantly reduced by the above-described surface treatments. Also, it was found that the Ca—P coating by phosphating treatment can improve the surface cytocompatibility and bioactivity of magnesium. Accordingly, biodegradable magnesium, the corrosion resistance and bioactivity of which are improved by surface coating, can be a preferable biomaterial.

Meanwhile, a stent consisting only of a magnesium layer have high in vivo corrosion rate, which lead to poor biostability and biocompatibility. In an example shown in FIG. 1, a stent is manufactured by forming an additional metal layer such as a titanium layer on a magnesium layer. However, in this example, if cracks occurred in the titanium layer due to corrosion or if crevices occurred in the titanium layer for other reasons, the magnesium layer was corroded more rapidly due to the cracks or crevices.

The foregoing discussion is to provide general background information, and does not constitute an admission of prior art.

SUMMARY

One aspect of the invention provides a stent, which comprises: a magnesium-dominant metallic layer; a ceramic layer formed over the magnesium-dominant metallic layer; and a magnesium-containing nonmetallic layer comprising a magnesium-containing compound and interposed between the metallic layer and the ceramic layer.

In the forgoing stent, the stent may comprise a wired structure, which has a cross-section comprising a core formed of the magnesium-dominant metallic layer, the nonmetallic layer surrounding the core, the ceramic layer surrounding the nonmetallic layer. The magnesium-dominant metallic layer may comprise magnesium in an amount of about 90 wt % or more. The magnesium-dominant metallic layer may additionally contain one or more elements selected from the group consisting of zinc (Zn), manganese (Mn), calcium (Ca), zirconium (Zr), yttrium (Y), molybdenum (Mo), niobium (Nb), tantalum (Ta), titanium (Ti), strontium (Sr), chromium (Cr), silicon (Si), phosphorus (P), nickel (Ni) and iron (Fe).

Still in the foregoing stent, the magnesium-containing nonmetallic layer may comprise at least one of magnesium fluoride ($MgF_2$) and magnesium oxide (MgO) as the magnesium-containing compound. The nonmetallic layer may have a thickness of about 0.05 μm to about 1.5 μm. The ceramic layer may comprise at least one of hydroxyapatite (HA) and titanium dioxide ($TiO_2$). The ceramic layer may have a thickness of about 0.1 μm to about 10 μm.

Another aspect of the invention provides a method of making a stent. The method comprises: providing a structure comprising a magnesium-dominant metallic layer and a magnesium-containing nonmetallic layer over the metallic layer; and forming a ceramic layer over the structure such that the nonmetallic layer is interposed between the metallic layer and the ceramic layer.

In the foregoing method, providing the structure may comprise providing the magnesium-dominant metallic layer; and sputtering a magnesium-containing compound to provide the magnesium-containing nonmetallic layer over the metallic layer. Providing the structure may comprise: providing a magnesium-dominant metallic material; and converting magnesium in surfaces of the magnesium-dominant metallic material to a magnesium-containing compound such that the magnesium-containing compound surrounds the magnesium-dominant metallic material. The magnesium-containing nonmetallic layer may comprise at least one of magnesium oxide (MgO) and magnesium fluoride ($MgF_2$). The magnesium oxide (MgO) may be formed by anodizing of the magnesium-dominant metallic material on surfaces thereof. The magnesium fluoride ($MgF_2$) may be formed by fluorination of the magnesium-dominant metallic material on surfaces thereof. The method may further comprise subsequent to converting, subjecting the structure to a temperature from about 200° C. to about 500° C. The ceramic layer may be formed by vacuum powder spraying of a ceramic material over the magnesium compound layer. The ceramic layer may be formed by applying a hydroxyapatite powder or titanium dioxide powder having a particle size of about 1 to about 5 μm over the magnesium-containing nonmetallic layer.

A further aspect of the invention provides a method of making a stent. The method comprises: providing a magnesium-dominant metallic material in a stent shape; forming a magnesium-containing compound layer over the magnesium-dominant metallic material; and forming a ceramic layer over the magnesium compound layer.

In the foregoing method, forming a magnesium-containing compound layer may comprise processing the magnesium-dominant metallic material to convert a portion of magnesium of the magnesium-dominant metallic material into a magnesium-containing compound thereby forming the magnesium-containing compound layer that surrounds the magnesium-dominant metallic material. Forming the magnesium-containing compound layer may comprise sputtering a magnesium-containing compound onto a surface of the magnesium-dominant metallic material.

An aspect of the present invention provides a biodegradable stent and a manufacturing method thereof, wherein the stent comprises a magnesium layer, a magnesium compound layer formed on the magnesium layer, and a ceramic layer formed on the magnesium compound layer.

Another aspect of the present invention provides a biodegradable stent and a manufacturing method thereof, wherein the stent is manufactured using a magnesium layer, a magnesium compound layer and a ceramic layer, which have excellent biocompatibility, whereby it can be degraded in vivo and byproducts resulting from the biodegradation thereof are harmless to the human body.

Still another aspect of the present invention provides a biodegradable stent and a manufacturing method thereof, wherein the thickness of a magnesium compound layer and ceramic layer of the stent is controlled, whereby the biodegradation rate of the stent can be controlled and initial corrosion thereof can be prevented.

Yet another aspect of the present invention provides a biodegradable stent and a manufacturing method thereof, wherein the outermost layer of the stent that will come into contact with cells is made of a ceramic layer which shows excellent cell adhesion and differentiation properties, whereby the stent has excellent biocompatibility and thus can reduce side effects during cell proliferation and differentiation.

A further aspect of the present invention provides a biodegradable stent comprising: a magnesium layer; a magnesium compound layer formed on the magnesium layer; and a ceramic layer formed on the magnesium compound layer.

BRIEF DESCRIPTION OF THE DRAWINGS

The above and other features and advantages of the present invention will be more clearly understood from the following detailed description taken in conjunction with the accompanying drawing, in which:

FIG. 19(b) shows a histological image of stained bone tissue which had come into contact with rod sample 2.

DETAILED DESCRIPTION OF EMBODIMENTS

Figure 2:
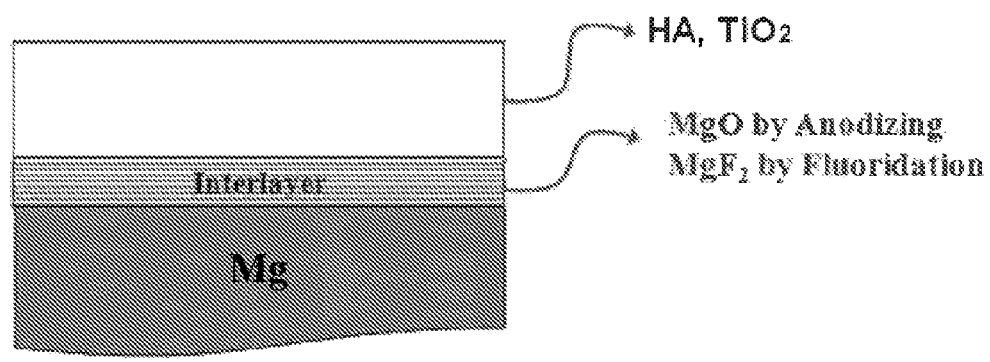
FIG. 2 is a cross-sectional view showing a biodegradable stent material according to one embodiment of the present invention.

Embodiments will be discussed in detail below. FIG. 2 shows the cross section of a stent material according to one embodiment of the present invention. Hereinafter, a biodegradable stent according to one embodiment of the present invention will be described in detail with reference to FIG. 2.

As shown in FIG. 2, a biodegradable stent according to one embodiment of the present invention comprises: a magnesium layer; a magnesium compound layer as an interlayer formed on the magnesium layer; and a ceramic layer formed on the magnesium compound layer.

Figure 1:
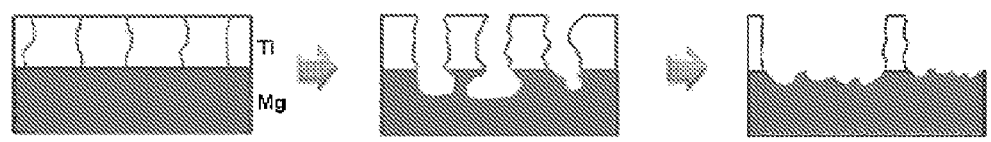
FIG. 1 schematically shows a process in which a prior-art stent material comprising a titanium layer formed on a magnesium layer is corroded.

Due to this structure, unlike an example shown in FIG. 1, magnesium can be prevented from being easily corroded at an initial stage, even if cracks or crevices occur in the ceramic layer. This is because magnesium is degraded after the ceramic layer and the magnesium compound layer had been degraded. Also, because the ceramic layer is formed as the outermost layer, the stent may have better biocompatibility.

Hereinafter, each layer of the stent will be described in detail.

Magnesium Layer

The magnesium layer or magnesium-dominant metallic layer is preferably made of a magnesium-dominant metallic material, which contains more than about 90% magnesium, and more preferably more than about 99%. This is because magnesium ions resulting from the degradation of magnesium is harmless to the human body and can be beneficial for bone growth.

Meanwhile, the magnesium layer may contain trace elements within a range harmless to the human body. For example, the magnesium layer may further contain one or more elements selected from the group consisting of zinc (Zn), manganese (Mn), calcium (Ca), zirconium (Zr), yttrium (Y), molybdenum (Mo), niobium (Nb), tantalum (Ta), titanium (Ti), strontium (Sr), chromium (Cr), silicon (Si), phosphorus (P), nickel (Ni) and iron (Fe). However, the content of such elements is preferably less than about 10%.

This is because, if the content of the above elements in the magnesium layer is less than 10%, harmful effects to the human body and adverse effect to the properties of magnesium in vivo of the ions of the elements, which are released by corrosion, can be reduced.

The magnesium layer generally has a thickness of about 50 to about 500 μm, but it should be noted that the thickness of the magnesium layer is not necessarily limited thereto and can vary depending on the user's intention or the specific configuration of the stent.

Magnesium Compound Layer

The magnesium compound layer or magnesium-containing nonmetallic layer is present as an interlayer between the magnesium layer and the ceramic layer, and thus serves to prevent the corrosion of the magnesium layer, even when cracks or crevices occur in the ceramic layer.

The magnesium compound layer or magnesium-containing nonmetallic layer contains one or more magnesium-containing compounds, which include magnesium fluoride ($MgF_2$) and magnesium oxide (MgO). Particularly, the magnesium compound layer is preferably made of magnesium fluoride ($MgF_2$).

The magnesium compound layer has a thickness of about 0.05 to about 1.5 μm in one embodiment, and about 0.4 to about 1 μm in another embodiment, in view of controlling the degradation rate of the stent.

The magnesium compound layer thicker than about 0.05 μm can delay the corrosion thereof proceeding along the cracks or crevices of the ceramic layer, and thus, the magnesium compound layer can effectively prevent or delay the corrosion of the magnesium layer. The magnesium compound layer thinner than about 1.5 μm can reduce occurrence of cracks or crevice during the formation of the magnesium compound layer, and thus the magnesium compound layer can effectively prevent or delay the corrosion of the magnesium layer.

In certain embodiments, the thickness of the magnesium compound layer is about 0.05 μm, about 0.15 μm, about 0.25 μm, about 0.3 μm, about 0.35 μm, about 0.4 μm, about 0.43 μm, about 0.46 μm, about 0.5 μm, about 0.52 μm, about 0.55 μm, about 0.58 μm, about 0.6 μm, about 0.63 μm, about 0.66 μm, about 0.7 μm, about 0.73 μm, about 0.77 μm, about 0.8 μm, about 0.85 μm, about 0.9 μm, about 0.95 μm, about 1 μm, about 1.1 μm, about 1.2 μm, about 1.3 μm, and about 1.5 μm. In some embodiments, the thickness has a range defined by two of the foregoing thicknesses.

Ceramic Layer

The ceramic layer is disposed as the outermost layer of the stent, which comes into contact with cells, and thus serves to allow the stent of one embodiment of the present invention to have excellent biocompatibility, that is cell adhesion and differentiation abilities.

The ceramic layer is characterized in that it is made of one or more selected from among hydroxyapatite (HA) and titanium dioxide ($TiO_2$). Particularly, it is preferably made of hydroxyapatite.

The reason for this is as follows. Because hydroxyapatite is a natural inorganic material similar to a bone-forming material, it has properties very similar to biomaterials and also excellent blood compatibility, and thus blood does not coagulate on the surface of the hydroxyapatite layer. Also, it has excellent cell compatibility, and thus causes little or no side effects during cell proliferation and differentiation.

The ceramic layer has a thickness of about 0.1 to about 10 μm in one embodiment, and about 1 to about 5 μm in another embodiment, in view of controlling the degradation rate of the stent.

The ceramic layer thicker than about 0.1 μm can delay the corrosion of the magnesium compound layer even though there are cracks or crevices in the ceramic layer. Further, the ceramic layer thinner than about 10 μm can avoid dissociation or detachment due to the difference in elastic modulus from the magnesium layer when the stent is inserted and expanded in blood vessels, and thus the corrosion of the stent proceeds can be effectively delayed.

In certain embodiments, the thickness of the ceramic layer is about 0.1 μm, about 0.5 μm, about 0.7 μm, about 1.0 μm, about 1.3 μm, about 1.5 μm, about 1.7 μm, about 2 μm, about 2.2 μm, about 2.4 μm, about 2.7 μm, about 3 μm, about 3.2 μm, about 3.4 μm, about 3.6 μm, about 3.9 μm, about 4.2 μm, about 4.6 μm, about 5 μm, about 6 μm, about 7 μm, about 8 μm, and about 10 μm. In some embodiments, the thickness has a range defined by two of the foregoing thicknesses.

Meanwhile, in the formation of the biodegradable stent according to one embodiment of the present invention, the thickness of any one of the magnesium compound layer and the ceramic layer can be controlled, thus controlling a period in which the stent is degraded in vivo.

Particularly, it is to be understood that the biodegradable stent according to one embodiment of the present invention can be degraded in vivo within a period of about 1 to about 6 months depending on the user's intention or its intended therapeutic purpose and can be designed such that it can maintain sufficient mechanical strength during the therapeutic period.

Although FIG. 2 shows only the surface portion of the biodegradable stent according to one embodiment of the present invention, it should be noted that a biodegradable stent according to one embodiment of the present invention can comprise a magnesium layer at the middle portion, a magnesium compound layer on both surfaces of the magnesium layer, and a ceramic layer on the surface of the magnesium compound layer, which is opposite to the magnesium layer, such that the magnesium layer or the magnesium compound layer does not constitute the outermost layer of the stent, and the region to which the magnesium compound layer or the ceramic layer is applied can change depending on the user's intention or the therapeutic purpose of the stent.

Figure 3:
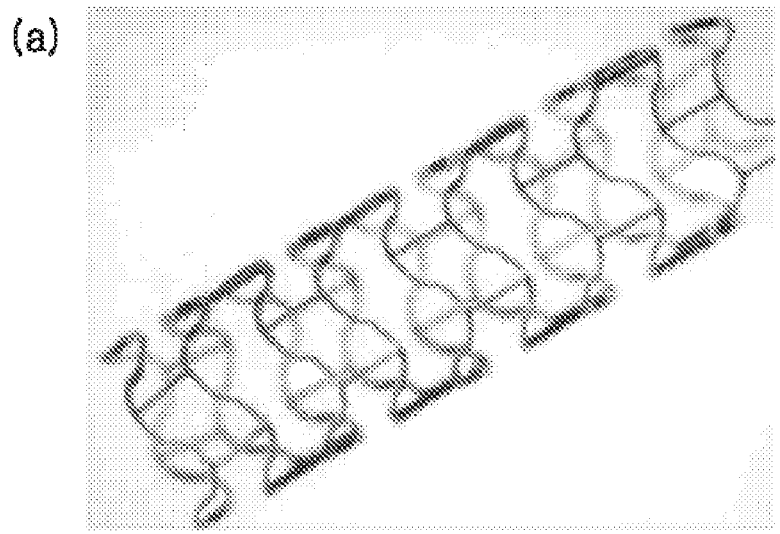
FIGS. 3(*a*), 3(*b*) and 3(*c*) illustrate the structure and configuration of stents according to one embodiment of the present invention.
Figure 3:
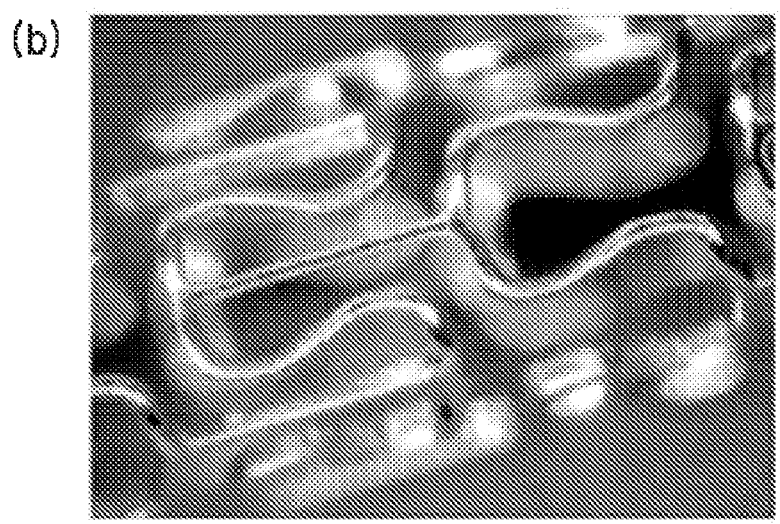
Figure 3:
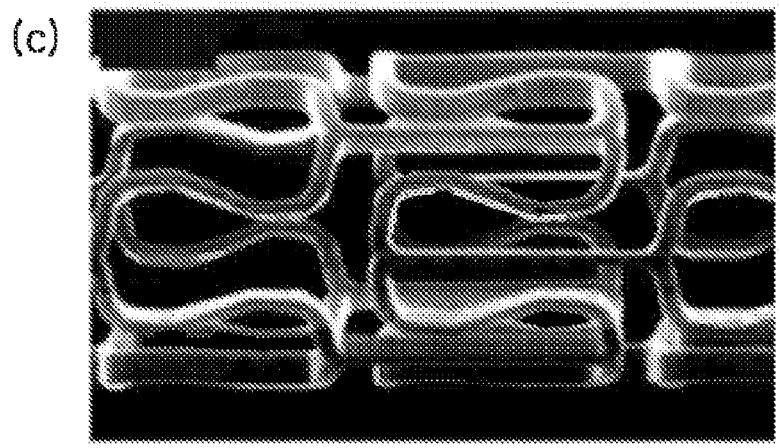

FIG. 3 illustrates the structure and configuration of a stent according to one embodiment. As shown in FIG. 3, it should be noted that the structure of the biodegradable stent according to one embodiment of the present invention may have various structures depending on the user's intention or its therapeutic purposes and is not necessarily limited to a specific configuration.

In another aspect, one embodiment of the present invention provides a method for manufacturing a biodegradable stent, the method comprising the steps of: (1) forming a magnesium compound layer on a magnesium layer; and (2) forming a ceramic layer on the magnesium compound layer.

Hereinafter, each step of the method in accordance with one embodiment of the present invention will be described in detail.

Forming Magnesium Compound Layer on Magnesium Layer

The magnesium compound layer is preferably made of one or more selected from among magnesium fluoride ($MgF_2$) and magnesium oxide (MgO).

According to one embodiment of the present invention, the magnesium compound layer is characterized in that it is made of magnesium fluoride ($MgF_2$). Herein, although the method of forming the magnesium fluoride layer on the magnesium layer is not specifically limited, a physical deposition method such as sputtering, in addition to a chemical treatment method using a chemical substance, may be used to form the magnesium fluoride layer. Preferably, the magnesium fluoride ($MgF_2$) layer is formed by fluorination.

Specifically, when the magnesium compound layer is made of magnesium fluoride, it can be formed by fluorination. For example, the magnesium fluoride layer can be formed on the magnesium layer by immersing the magnesium layer in a hydrogen fluoride (HF) solution. Meanwhile, because this fluorination can be carried out using any known method, the detailed description thereof will be omitted herein.

According to another embodiment of the present invention, the magnesium compound layer is characterized in that it is made of magnesium oxide (MgO). Herein, although the method of forming the magnesium oxide layer on the magnesium layer is not specifically limited, a physical deposition method such as sputtering, in addition to a chemical treatment method using a chemical substance, may be used to form the magnesium oxide layer. Preferably, the magnesium oxide (MgO) layer is formed by anodizing.

Specifically, if the magnesium compound layer is the magnesium oxide layer, the magnesium oxide layer can be formed on the magnesium layer by treating the surface of the magnesium layer by anodizing. Meanwhile, because this anodizing can be carried out using any known method, the detailed description thereof will be omitted herein.

In order to increase the compactness of the magnesium oxide layer, heat treatment may additionally be carried out. If the compactness of the magnesium oxide layer is high, the degradation rate of the magnesium oxide layer can be reduced. Thus, it should be noted that either of (a) whether heat treatment is carried out or (b) the heat treatment conditions may be selected depending on the user's intention or the desired degradation rate.

For example, after the magnesium oxide layer has been formed, it is preferably heat-treated at a temperature between about 200° C. and about 500° C. for about 1 to about 3 hours. When the heat-treatment temperature is higher than about 200° C., heat sufficient to increase the compactness of the magnesium oxide layer can be supplied, and when the heat-treatment temperature is lower than about 500° C., the occurrence of cracks or crevices in the magnesium oxide layer can be avoided.

Forming Ceramic Layer on Magnesium Compound Layer

The ceramic layer is characterized in that it is made of one or more selected from among hydroxyapatite (HA) and titanium dioxide ($TiO_2$).

This ceramic layer is preferably formed by vacuum powder spraying.

Herein, the smaller the particle size of the ceramic layer material, the more compact coating can be formed. Thus, powder of suitable particle size can be selected depending on the user's intention or the intended use. For example, the ceramic layer is preferably formed using hydroxyapatite or titanium dioxide powder having a particle size of about 1 to about 5 μm. In this case, there are advantages in that the ceramic layer can be formed as a relatively compact coating layer without heat treatment and it is easy to control the thickness of the ceramic layer.

In another aspect, one embodiment of the present invention relates to a method for manufacturing a biodegradable stent, the method comprising the steps of: (a) forming magnesium into a stent shape as a magnesium layer; (b) forming a magnesium compound layer on the magnesium layer; and (c) forming a ceramic layer on the magnesium layer.

It is to be understood that the step of forming the stent shape using magnesium is a step of forming stents of various shapes using any known method according to the user's intention or the therapeutic purpose and is not necessarily limited to a specific method. Because the remaining two steps have already been described above, the detailed description thereof will be omitted herein.

The stent manufactured according to the above-described method can be used in applications known in the art, such as vasodilation.

According to one embodiment of the present invention, a stent is manufactured using a magnesium layer, a magnesium compound layer and a ceramic layer, which have excellent biocompatibility, and thus the stent can be degraded in vivo and the production of byproducts harmful to the human body, which result from the biodegradation of the stent, can be further reduced.

Also, according to one embodiment of the present invention, by controlling the thickness of the magnesium compound layer and ceramic layer of the stent, the biodegradation rate of the stent can be controlled according to the user's intention, and the initial corrosion of the stent can be more easily prevented.

Also, according to one embodiment of the present invention, the outermost layer of the stent, which comes into contact with cells, consists of the ceramic layer having excellent cell adhesion and differentiation abilities, and thus the side effects of the stent during cell proliferation and differentiation can be further reduced.

Hereinafter, examples will be provided for a better understanding of embodiments of the present invention. It is to be understood, however, that these examples are for illustrative purposes only and are not to be construed to limit the scope of the present invention.

Manufacture Example 1

1) A magnesium substrate manufactured from a magnesium ingot (99.9% Mg) was prepared.

2) A magnesium fluoride ($MgF_2$) layer was formed on the magnesium substrate by fluorination. Specifically, the magnesium substrate was immersed in a 48 wt % hydrogen fluoride aqueous solution for 24 hours, thereby forming a 1-μm-thick magnesium fluoride layer on the magnesium substrate.

Figure 4:
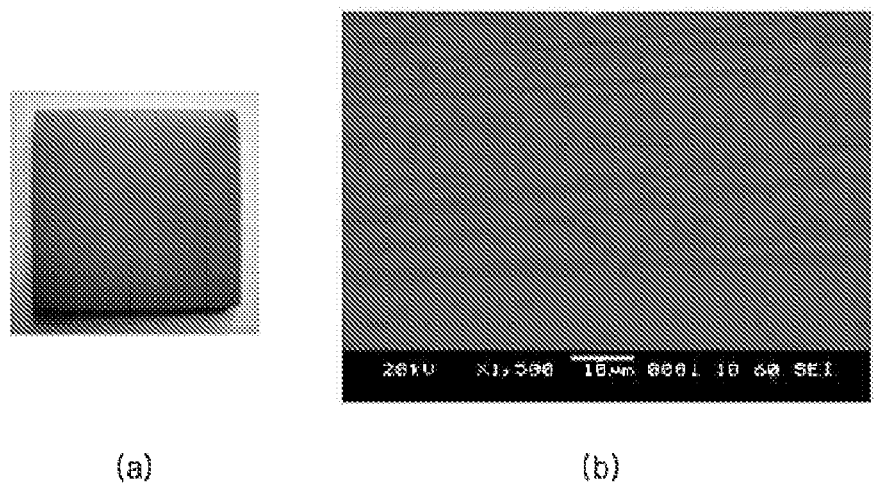
FIG. 4 shows photographs of the surface of a magnesium fluoride layer of a biodegradable stent according to one embodiment of the present invention ((a): surface photograph, and (b): SEM photograph)

FIG. 4 shows photographs of the magnesium fluoride layer formed by the above method. Namely, FIG. 4 shows photographs of the surface of the magnesium fluoride layer of the stent according to one embodiment of the present invention ((a): surface photograph; and (b): SEM photograph).

3) Then, a hydroxyapatite layer was formed in the magnesium fluoride layer by vacuum powder spraying. Specifically, fine hydroxyapatite powder was heat-treated at 1100° C. for 1 hour. The heat-treated hydroxyapatite powder was mixed with oxygen gas and sprayed into a vacuum chamber containing the substrate through a nozzle by the difference in pressure therebetween. Herein, the pressures of the heat-treatment chamber and the vacuum chamber were 80 kPa and 900 Pa. In this way, a 5-μm-thick hydroxyapatite layer was formed on the magnesium fluoride layer.

Figure 5:
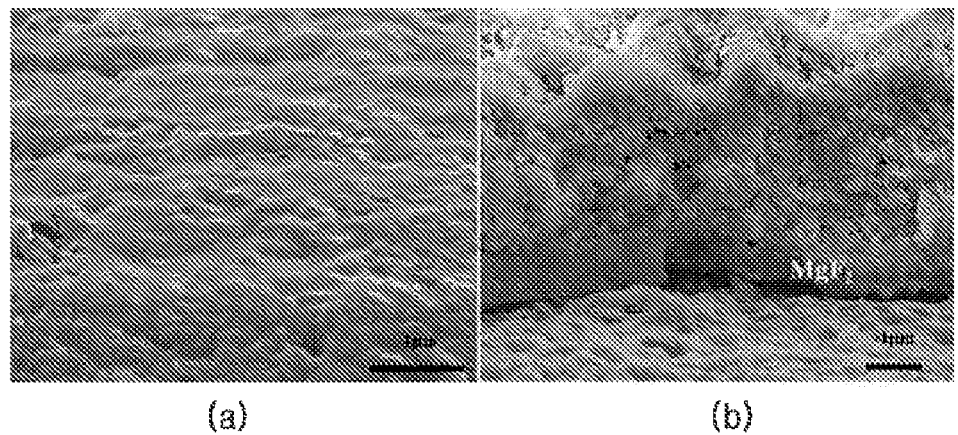
FIGS. 5(*a*) and 5(*b*) show photographs of the surface and cross section of a stent manufactured in Manufacture Example 1, respectively.

FIG. 5 shows photographs of the surface and cross section of the stent formed according to the above method. Namely, FIG. 5 shows photographs of the surface and cross section of the stent manufactured in Manufacture Example 1.

Manufacture Example 2

1) A magnesium substrate manufactured from a magnesium ingot (99.9% Mg) was prepared.

2) A magnesium oxide (MgO) layer was formed on the magnesium substrate by anodizing. Specifically, voltage was applied from a DC power supply across the magnesium substrate as an anode and stainless steel as a cathode in an electrolyte solution containing potassium hydroxide (KOH), potassium fluoride (KF) and trisodium phosphate ($Na_3PO_4$), thereby forming a 0.6-μm-thick magnesium oxide layer on the magnesium substrate.

Figure 6:
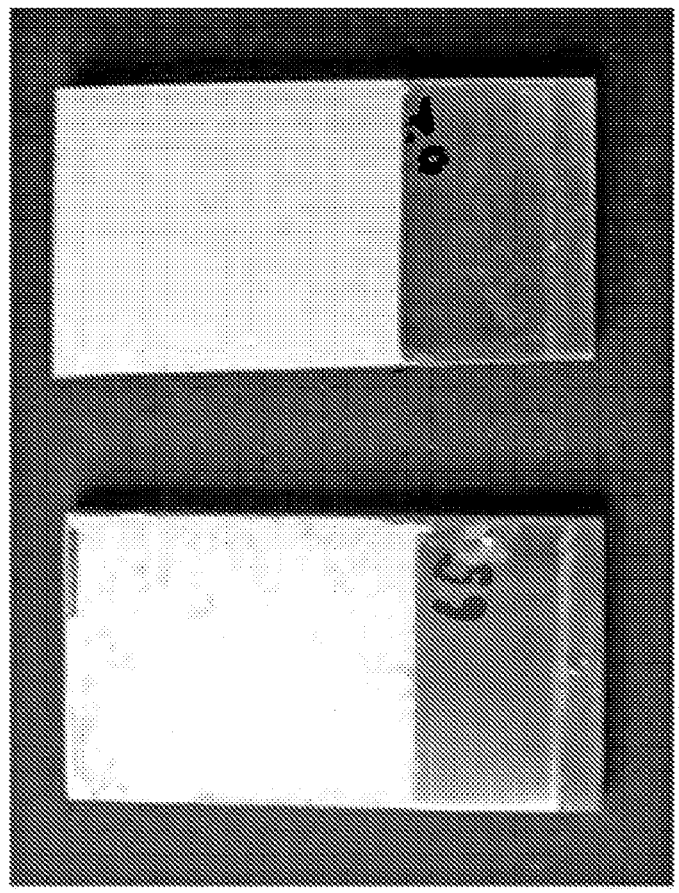
FIG. 6 shows current density and voltage during a process of forming a magnesium layer of a biodegradable stent according to one embodiment of the present invention.
Figure 6:
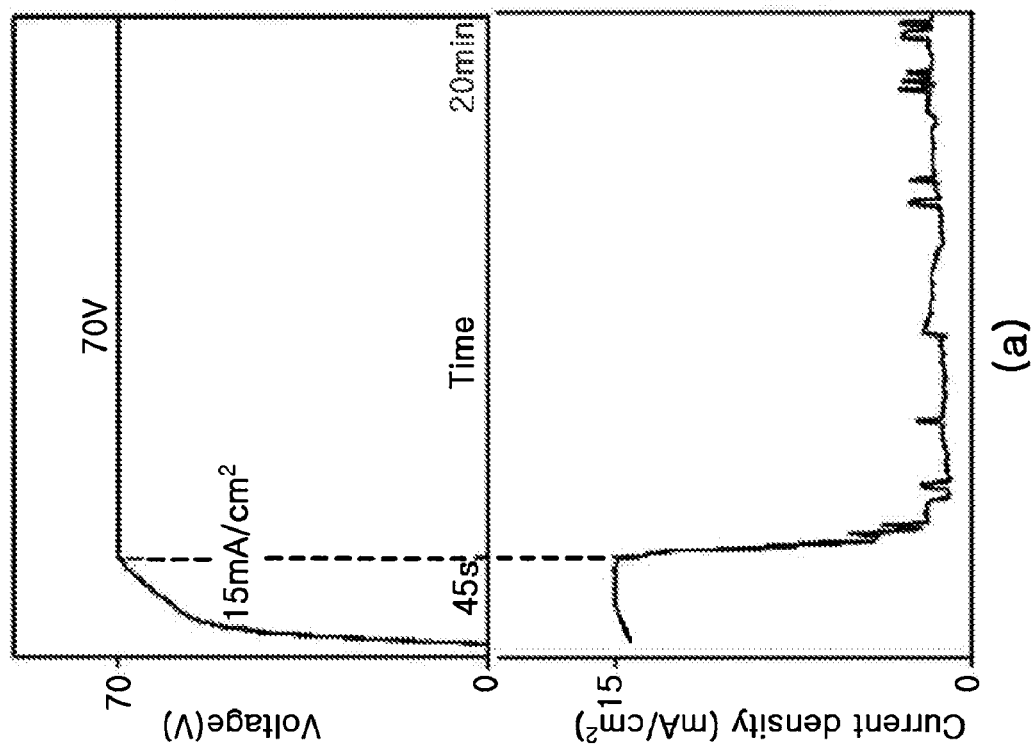

The thickness of the magnesium oxide layer can be controlled depending on the concentration of the electrolyte solution, the oxidation time, the intensity of electric current, etc. FIG. 6 shows a graph of current density and voltage measured during the formation of the magnesium oxide layer. Namely, FIG. 6 shows current density and voltage during the formation of the magnesium oxide layer of the stent according to one embodiment of the present invention.

Figure 7:
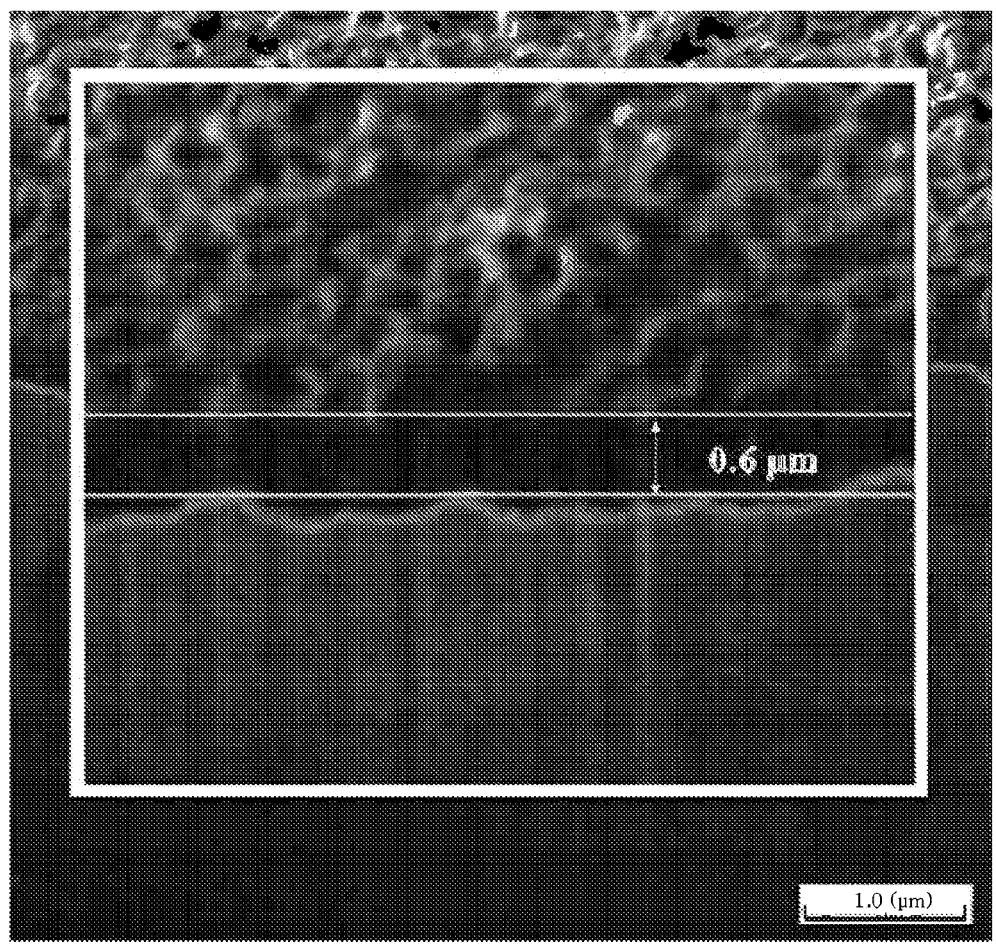
FIG. 7 is a photograph showing the cross section of a stent manufactured in Manufacture Example 2.

Meanwhile, FIG. 7 shows a photograph of the surface and cross section of the magnesium oxide layer formed on a magnesium substrate.

Figure 8:
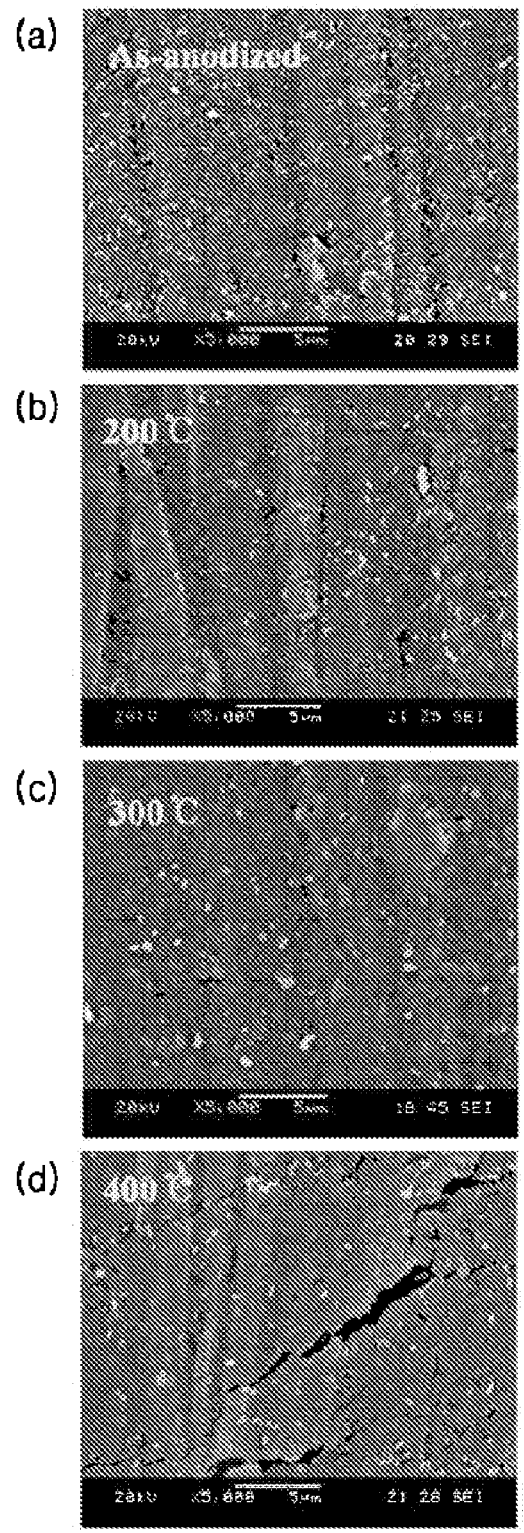
FIGS. 8(*a*), 8(*b*), 8(*c*) and 8(*d*) are photographs of the surface of a magnesium oxide layer of a stent according to one embodiment of the present invention.

3) To increase the compactness of the magnesium oxide layer, heat treatment was carried out as an additional process. Specifically, the magnesium oxide layer was heat-treated at 200° C., 300° C. and 400° C. for 1 hour at each temperature. FIG. 8 shows photographs of the magnesium oxide layers formed by the above method.

Test Example 1

For the magnesium layer (sample 1), magnesium layer/magnesium fluoride layer (sample 2) and magnesium layer/magnesium fluoride layer/hydroxyapatite layer (sample 3) produced in Manufacture Example 1, the weight loss caused by corrosion (see FIG. 9), the dissolution of magnesium ions (see FIG. 10), the alkalization (see FIG. 11) and the polarization curve (see FIG. 12) were measured in the following manner.
Weight Loss Caused by Corrosion 1.77 $cm^2$ of the surface of each of samples 1, 2 and 3 was exposed to simulated body fluid (SBF) solution at room temperature. The change in weight of each of samples 1, 2 and 3 with time was measured.
Dissolution of Magnesium Ions Each of samples 1, 2 and 3 was immersed in 100 mL of SBF solution, and the change in concentration of magnesium ions in the SBF solution with time was measured using ICP-AES.
Alkalization 1.77 $cm^2$ of the surface of each of samples 1, 2 and 3 was exposed to simulated body fluid (SBF) solution at room temperature. The change in pH of the SBF solution with time was measured.
Polarization Curve Using SBF as an electrolyte solution, a Pt electrode, a SCE electrode, and sample 1 or 3 as an electrode, the polarization curve was measured.

Test Example 2

Figure 13:
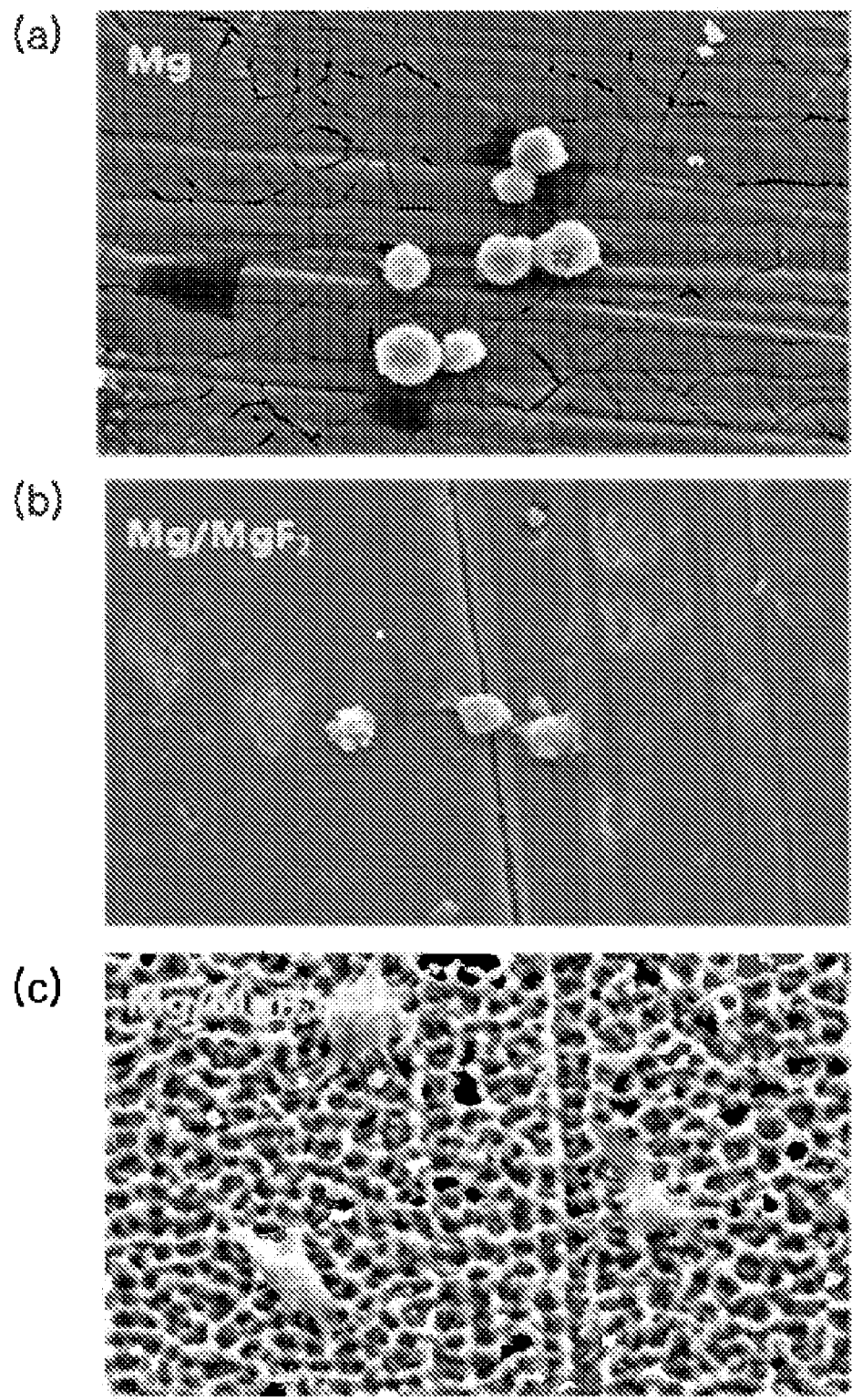
FIGS. 13(*a*), 13(*b*), 13(*c*), 14(*a*), 14(*b*) and 14(*c*) are photographs showing cell adhesion to stents having different layer structures.

Using the magnesium layer (sample 1), magnesium layer/magnesium fluoride layer (sample 2) and magnesium layer/magnesium fluoride layer/hydroxyapatite layer (sample 3) produced in Manufacture Example 1, cell adhesion (see FIGS. 13 and 14), cell proliferation (FIG. 15) and cell differentiation (see FIG. 16) were measured in the following manner.
Cell Adhesion (1) Pre-osteoblast cells were seeded onto the surface of each of samples 1, 2 and 3, and after 5 (five) hours, whether the cells adhered well to the sample surface was observed by SEM. The observation results are shown in FIG. 13.

Figure 14:
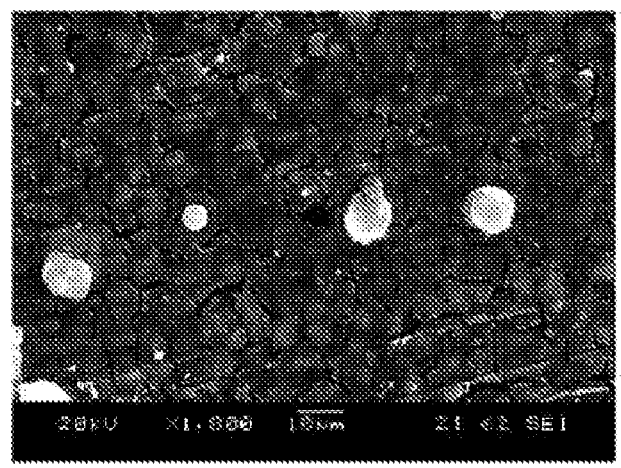
Figure 14:
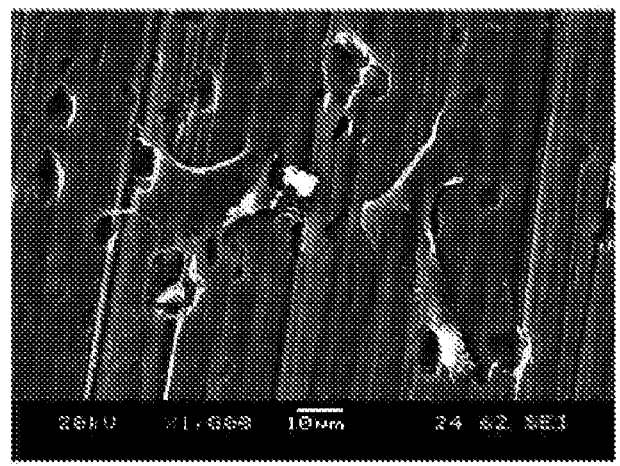
Figure 14:
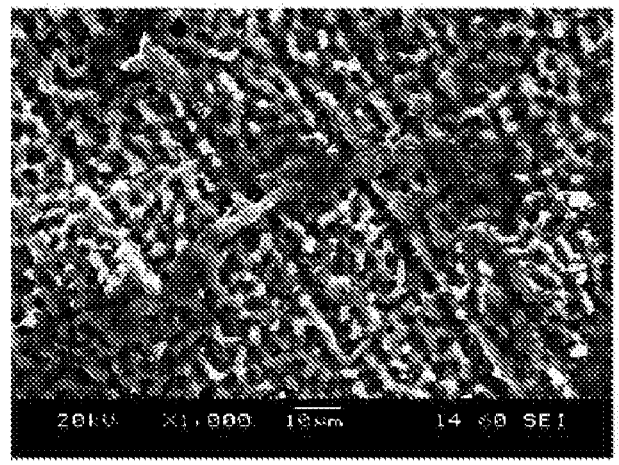

(2) Endothelial cells were seeded onto the surface of each of samples 1, 2 and 3, and after a given period of time, whether the cells adhered well to each sample surface was observed by SEM. The observation results are shown in FIG. 14.
Cell Proliferation Pre-osteoblast cells were seeded onto the surface of each of samples 1, 2 and 3, and after 5 (five) days, the viability of the pre-osteoblast cells on each sample surface was measured.
Cell Differentiation Pre-osteoblast cells were seeded onto the surface of each of samples 1, 2 and 3, and after 10 days, substances produced during the differentiation of the pre-osteoblast cells into osteoblast cells were spectrometrically measured and expressed in terms of alkaline phosphatase (ALP) activity.
<Concrete Examination>

Test Example 1 was carried out in order to compare the degree of corrosion of the magnesium layer (sample 1), the magnesium layer/magnesium fluoride layer (sample 2) and the magnesium layer/magnesium fluoride layer/hydroxyapatite layer (sample 3) produced in Manufacture Example 1.

Figure 9:
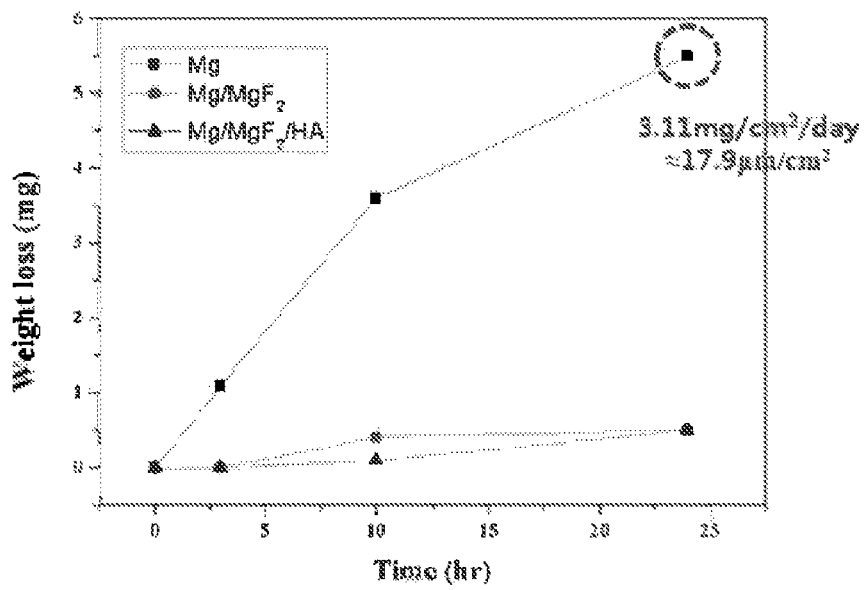
FIG. 9 is a graphic diagram showing the results obtained by conducting a test for the weight loss caused by corrosion in stents having different layer structures.

As can be seen in FIG. 9, sample 1 showed a rapid decrease in weight, unlike samples 2 and 3. Particularly, sample 1 showed a weight loss of 3.11 mg/cm$^2$ after 24 hours. On the other hand, samples 2 and 3 showed a weight loss of 0.2 mg/cm$^2$ after 24 hours.

Specifically, the weight loss by corrosion for 24 hours was about 11 times larger in the sample 1 than in the samples 2 and 3, suggesting that the initial corrosion of the magnesium layer/magnesium fluoride layer and the magnesium layer/magnesium fluoride layer/hydroxyapatite layer proceeded slower than the magnesium layer.

Figure 10:
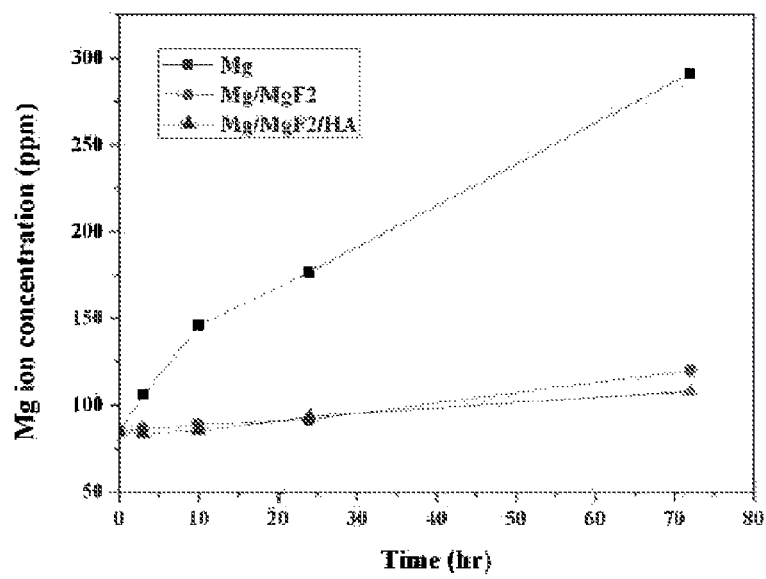
FIG. 10 is a graphic diagram showing the results obtained by measuring the dissolution of magnesium ions from stents having different layer structures.

As can be seen in FIG. 10, the concentration of magnesium ions in the SBF solution immersed with the sample 1 rapidly increased from the initial stage of the measurement, unlike samples 2 and 3. Particularly, after 70 hours, the concentration of magnesium ions was about 293 ppm for the SBF solution in which sample 1 was immersed, about 120 ppm for the SBF solution in which sample 2 was immersed, and about 110.5 ppm for the SBF solution in which sample 3 was immersed.

Specifically, when the initial concentration of magnesium ions was supposed to be about 80 ppm, the magnesium ion concentration increased by about 213 ppm in the case of sample 1 due to initial corrosion, also increased by about 40 ppm in the case of sample 2 due to progressive corrosion, and increased by about 30 ppm in the case of sample 3 due to progressive corrosion. This suggests that the initial corrosion of the magnesium layer/magnesium fluoride layer/hydroxyapatite layer and the magnesium layer/magnesium fluoride layer proceeded slower than the magnesium layer, and further that the corrosion of the magnesium layer/magnesium fluoride layer/hydroxyapatite layer proceeded slower than the magnesium layer/magnesium fluoride layer.

Figure 11:
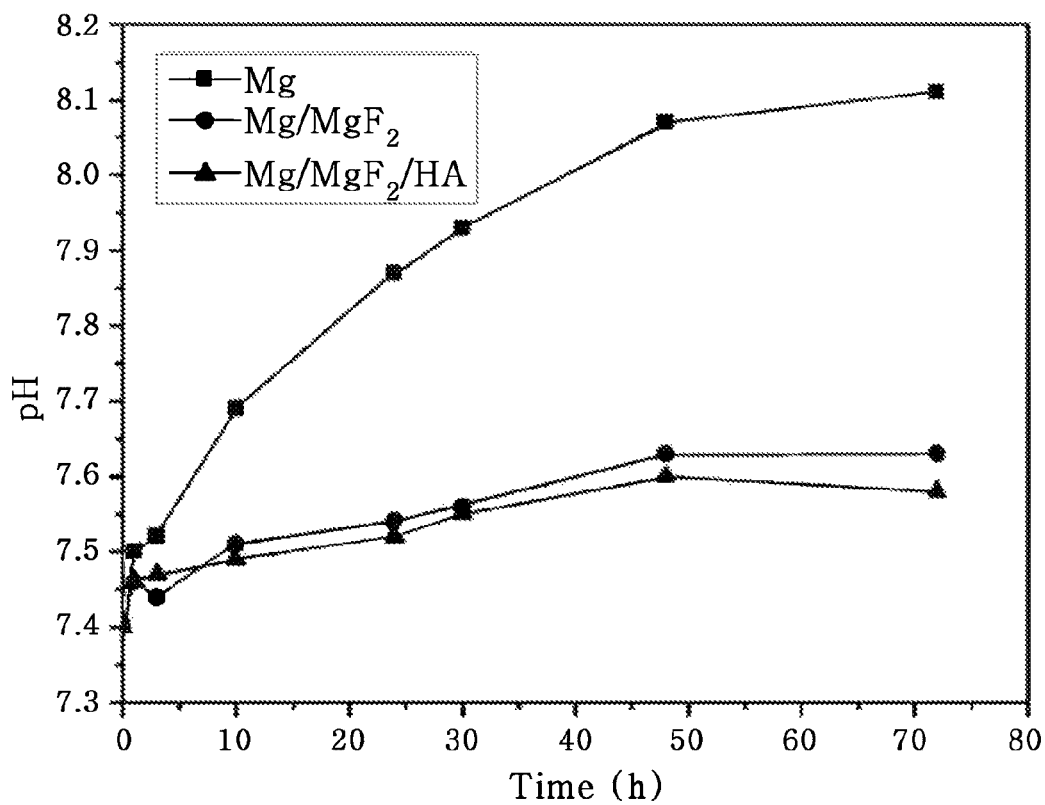
FIG. 11 is a graphic diagram showing the results obtained by measuring the alkalization of a solution for stents having different layer structures.

As can be seen in FIG. 11, after about 70 hours, the pH of the SBF solution, to which the sample 1 has been exposed, increased from 7.4 to 8.1, the pH of the SBF solution, to which sample 2 had been exposed, increased from 7.4 to 7.62, and the pH of the SBF solution, to which sample 3 had been exposed, increased from 7.4 to 7.58.

This increase in the pH of the SBF solution is attributed to the dissolution of magnesium ions caused by corrosion, and a greater increase in the pH means more rapid corrosion. Like the case of FIG. 9, the above results suggest that the initial corrosion of the magnesium layer/magnesium fluoride layer/hydroxyapatite layer and the magnesium layer/magnesium fluoride layer proceeded slower than that of the magnesium layer, and further that the magnesium layer/magnesium fluoride layer/hydroxyapatite layer proceeded slower than the magnesium layer/magnesium fluoride layer.

Figure 12:
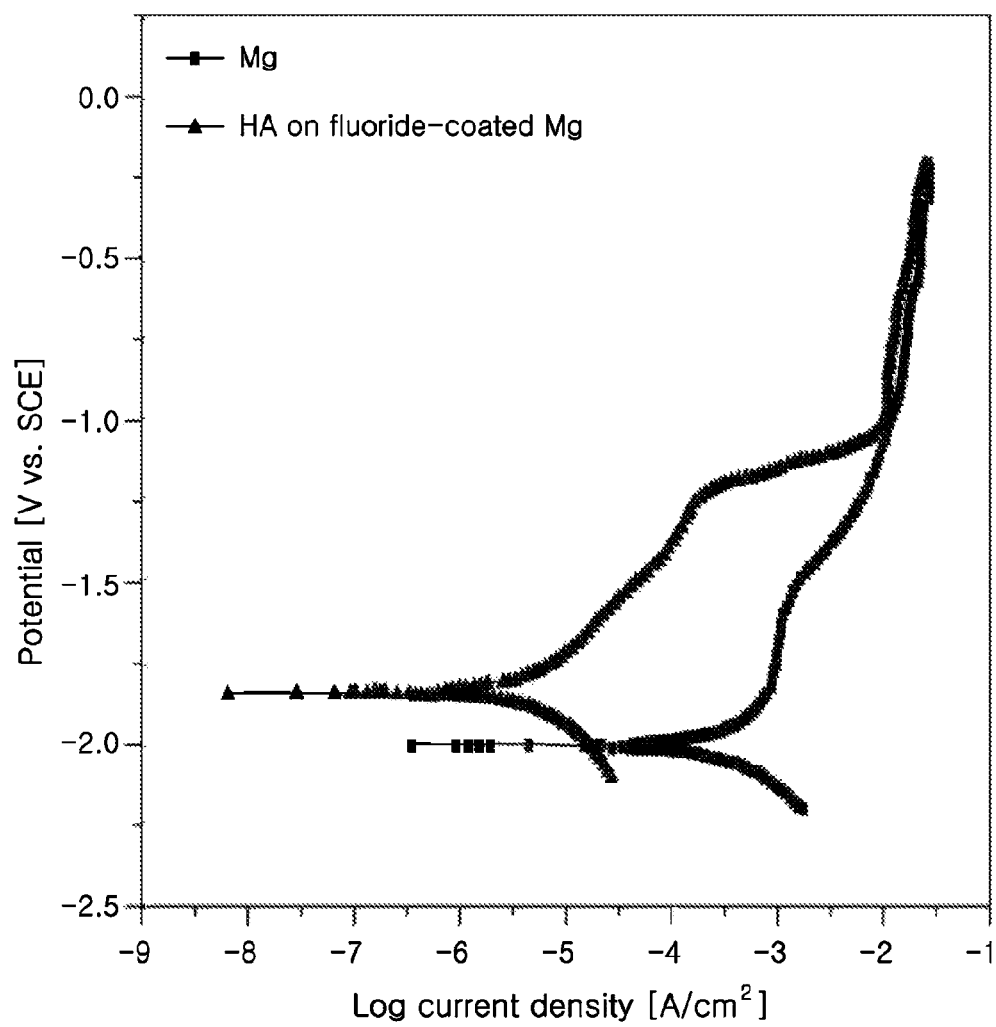
FIG. 12 is a graphic diagram showing the results obtained by measuring the polarization curves of stents having different layer structures.

As can be seen in FIG. 12, the polarization curve in the case in which sample 3 was used as an electrode was closer to the upper and right sides of the graph compared to the case in which sample 1 was used as an electrode. The polarization curve indicates the corrosion properties of materials, and if the polarization curve is closer to the upper and right sides, this means higher corrosion resistance. Thus, the graph of FIG. 12 indicates that the corrosion of the magnesium layer/magnesium fluoride layer/hydroxyapatite layer proceeds slower than that of the magnesium layer.

Test Example 2 was carried out in order to compare the cell compatibilities (such as cell adhesion, cell proliferation and cell differentiation) of the magnesium layer (sample 1), the magnesium layer/magnesium fluoride layer (sample 2) and the magnesium layer/magnesium fluoride layer/hydroxyapatite layer (sample 3) produced in Manufacture Example 1.

As can be seen in FIG. 13, pre-osteoblast cells which did not adhere to the surface of sample 1 agglomerated into round shapes. Also, several pre-osteoblast cells were spread out slightly across the surface of sample 2. In contrast, pre-osteoblast cells adhered to the surface of sample 3 while being spread out wide across the surface of sample 3.

As can be seen in FIG. 14, endothelial cells were present separately on the surface of sample 1 without adhering to the surface of the sample. On the other hand, endothelial cells adhered to the surface of sample 2 while they were widely spread on the surface of sample 2. Also, endothelial cells adhered substantially integrally to the ceramic layer on the surface of sample 3.

On the basis of such photographs, it can be seen that cells do not adhere well to the magnesium layer and that cells adhere well to the magnesium layer/magnesium fluoride layer/hydroxyapatite layer.

Figure 15:
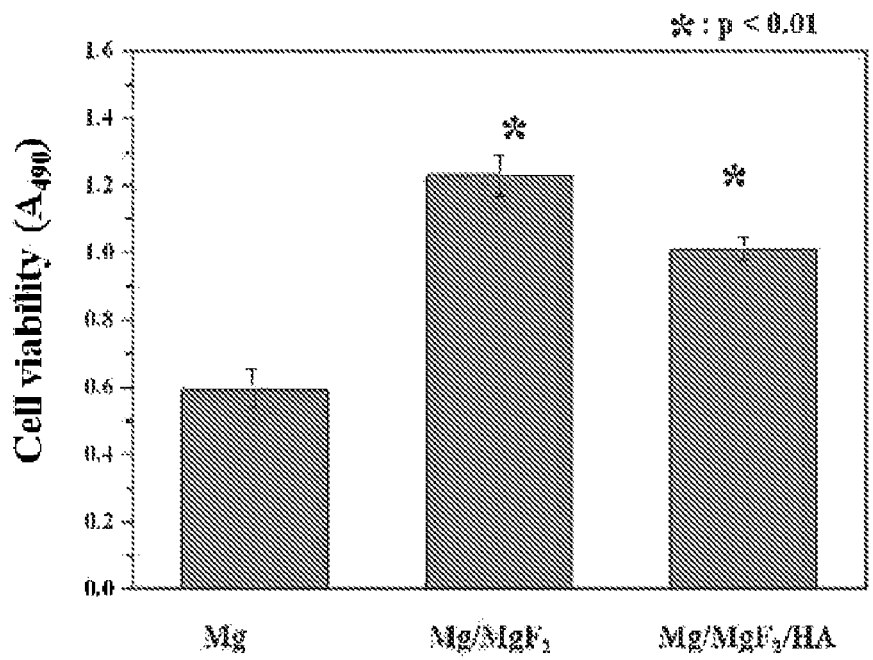
FIG. 15 is a graphic diagram showing cell proliferation on stents having different layer structures.

As can be seen in FIG. 15, there was cell proliferation on sample 2 and there was more cell proliferation on sample 3. On the other hand, sample 1 showed the lowest cell proliferation. The results of FIG. 15 suggest that the proliferation of cells showed no great difference between the magnesium layer/magnesium fluoride layer/hydroxyapatite layer and the magnesium layer/magnesium fluoride layer and showed a great difference between these two structures and the magnesium layer.

Figure 16:
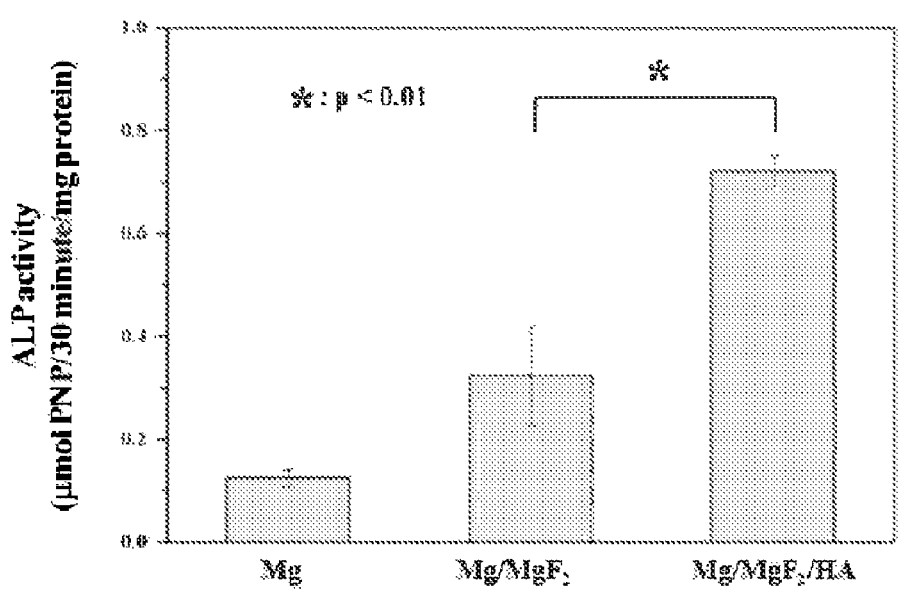
FIG. 16 is a graphic diagram showing cell differentiation on stents having different layer structures.

As can be seen in FIG. 16, the ALP activity was about 0.12 for sample 1, about 0.33 for sample 2, and 0.72 for sample 3.

Namely, it can be seen that the pre-osteoblast cells seeded onto the surface of sample 3 showed the highest differentiation into osteoblast cells during the culture period of 10 days. The alkaline phosphatase activity of the magnesium layer/magnesium fluoride layer/hydroxyapatite was higher than that of the magnesium layer/magnesium fluoride layer and was significantly higher than the magnesium layer (*$P<0.01$).

Test Example 3

In Vivo Animal Test

A rod sample 1 made of more than 99% magnesium (hereinafter, referred as to rod sample 1) was prepared. Also, according to the method of Manufacture Example 1, a rod sample comprising a magnesium fluoride layer/hydroxyapatite layer coated on magnesium (hereinafter referred to as rod sample 2) was prepared. The prepared rod samples all had a diameter of 45 mm and a length of 10 mm.

Figure 17:
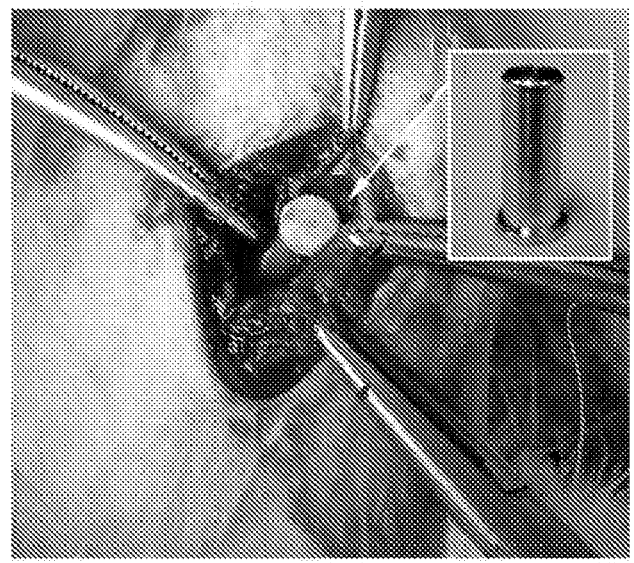
FIG. 17 is a photograph showing rod sample 1 and a process of implanting the rod sample 1 into test animals.

Using such rod samples 1 and 2, an in vivo animal test was carried out. Animals used in the test were nine male New Zealand white rabbits (12 weeks old, average weight 3 kg) (hereinafter referred to as the test animals). FIG. 17 is a photograph showing rod sample 1 and a process of implanting rod sample 1 into the test animals.

First, the test animals were systemically anesthetized with a combination of 1.5 cc of 2% Xylazine HCl (Rompun, Bayer Korea, Korea) and 0.5 cc of Tiletamine HCl (Zoletil, Virbac lab, France) and Lidocaine (Yuhan Corporation, Korea), and 1:100,000 epinephrine was injected as the local anesthesia. Rod samples 1 and 2 were implanted into the femoral defects that drilled into the bone using a hand piece drill. After surgery, the wounds were sutured with Surgisorb (Samyang Ltd, Korea), and then cephradine (Bayer Korea, Korea), an antibiotic, was injected into the rabbits for 3 days.

Figure 18:
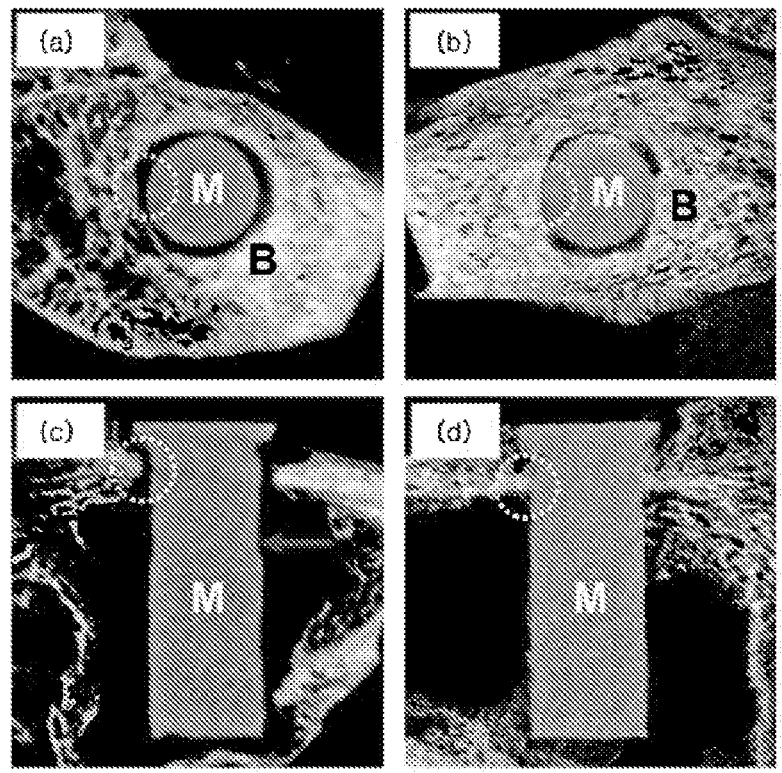
FIGS. 18(*a*) and 18(*c*) are reconstructed micro-CT images showing the morphology of rod sample 1 and bone tissue four weeks after implantation of rod sample 1, and FIGS. 18(*b*) and 18(*d*) are reconstructed micro-CT images showing the morphology of rod sample 2 and bone tissue two weeks after implantation of rod sample 2.

All the test animals were observed during 4 weeks after the implant surgery. The harvested bone tissues were scanned using a micro-CT (Skyscan 1183 X-ray Micro-tomography System, Skyscan, Kontich, Belgium) with a 1.0 mm aluminum filter at a resolution of 35 μm, a voltage of 100 kV, and a current of 60 μA in order to 3-dimensionally observe the morphology of rod samples 1 and 2 and the bone tissues. Subsequently, the images were reconstructed using a commercial program. Based on the reconstructed images, the morphologies of rod samples 1 and 2 and the bone tissues in the cortical area were 3-dimensionally observed using Data viewer (Skyscan, Kontich, Belgium). Such images are shown in FIG. 18.

Figure 19:
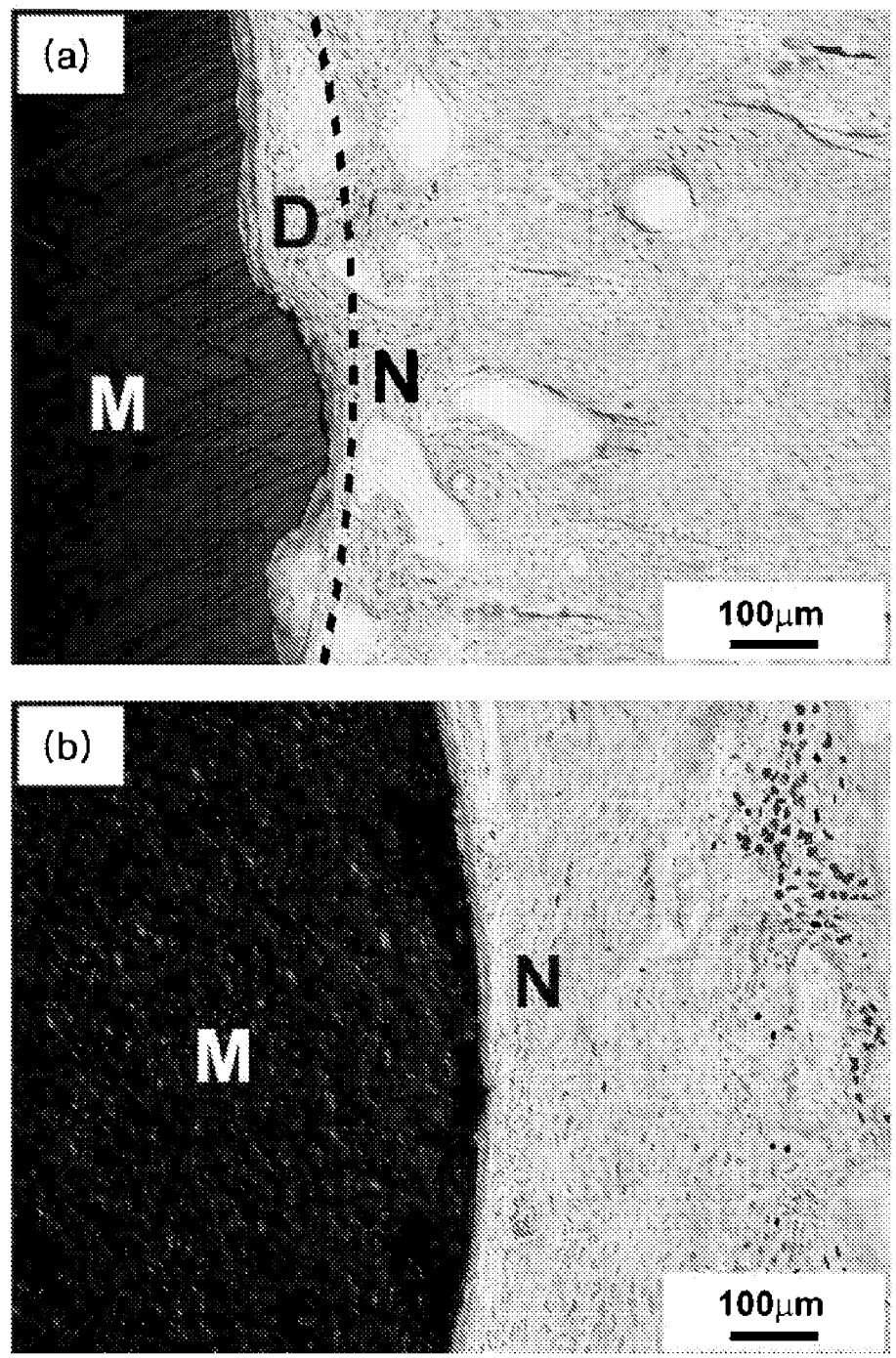
FIG. 19(*a*) shows a histological image of stained bone tissue which had come into contact with rod sample 1.

After the micro-CT scanning, the extracted bone samples were fixed in a neutral 10% formaldehyde solution, and tissue blocks were formed using the resin. The microscopic images of the trichrome and haematoxylin-eosin stained sections were obtained using Axioskop microscopy (Olympus BX51, Olympus Corporation, Tokyo, Japan). The histological images of stained bone tissues which had come into contact with rod samples 1 and 2 are shown in FIG. 19.

Figure 20:
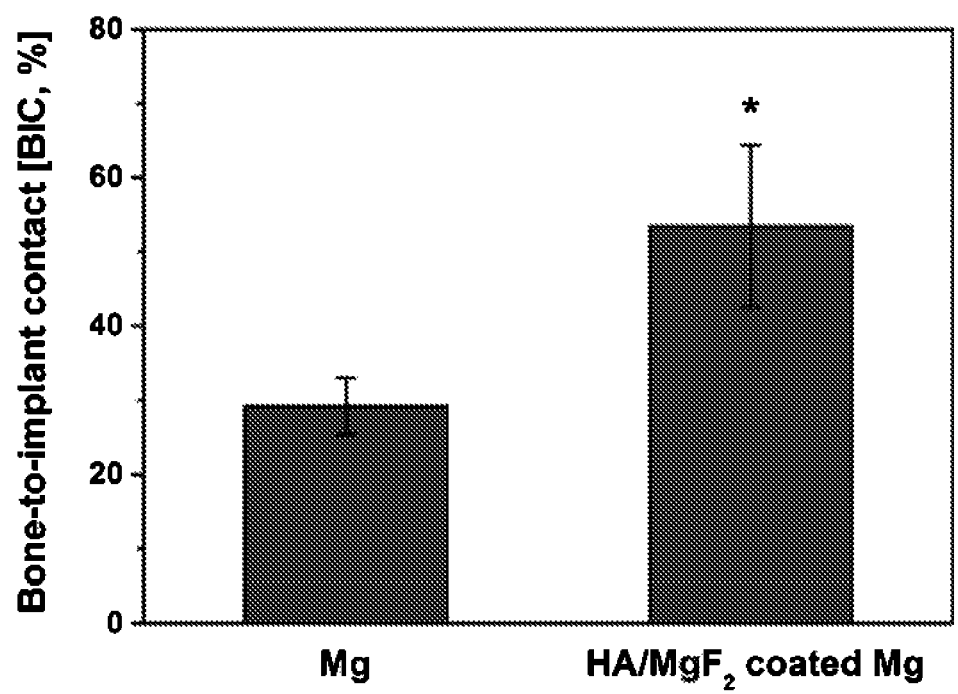
FIG. 20 is a graphic diagram showing the bone-to-implant contact ratios of rod samples 1 and 2 in the cortical area.

The bone-to-implant contact (BIC) ratios were calculated from the images using a digital image analysis program (SPOT, Diagnostic instrument, Inc., MI, USA). The bone-to-implant contact ratios for rod samples 1 and 2 are shown in FIG. 20.

All the experiments were performed more than three times, and the experimental results were expressed as mean±standard deviation (SD). The difference between the two groups was determined using a one-way analysis of variance (ANOVA), and a $p<0.05$ was considered a statistically significant difference.

<Concrete Examination: In Vivo Animal Test>

The in vivo behaviors of the magnesium implants were observed using the rabbit femoral defect model. Rod samples 1 and 2 were implanted into each femur of the test animal. After 4 weeks for implantation, the rod samples were removed, and the micro-CT images of the retrieved samples were shown in FIG. 18.

FIGS. 18(a) and 18(c) are reconstructed micro-CT images showing the morphology of bone tissue and rod sample 1 four weeks after implantation of the rod sample 1, and FIGS. 18(b) and 18(d) are reconstructed micro-CT images showing the morphology of bone tissue and rod sample 2 two weeks after implantation of rod sample 2. In FIG. 18, M: rod sample; B: bone tissue; and dotted circle: bone-to-implant contact.

As can be seen in FIGS. 18(a) and 18(c), the width of rod sample 1 was partially reduced due to the corrosion of magnesium. Also, the gap between rod sample 1 and the bone tissue in the cortical bone tissue occurred. On the other hand, as can be seen in FIGS. 18(b) and 18(d), the morphology of rod sample 2 was maintained intact, and little or no gap between rod sample 2 and the bone tissue in the cortical bone tissue occurred, and also rod sample 2 showed a good bone-to-implant contact compared to rod sample 1. The reason for this is because the coated magnesium fluoride layer/hydroxyapatite layer prevented the corrosion of magnesium in vivo.

FIG. 19(a) shows a histological image of stained bone tissue which had come into contact with rod sample 1, and FIG. 19(b) shows a histological image of stained bone tissue which had come into contact with rod sample 2. In FIG. 19, M: rod sample; N: new bone tissue; and D: degraded magnesium area.

As can be seen in FIG. 19, although newly formed bone tissue was observed around the surfaces of both rod samples 1 and 2, a more important bone contact was observed in rod sample 2 without degradation of magnesium.

FIG. 20 is a graphic diagram showing the bone-to-implant contact ratios of rod samples 1 and 2 in the cortical area. This graph was measured using an image analysis program on the basis of the histological images.

As can be seen in FIG. 20, four weeks after implantation of the samples, rod sample 2 showed a very high bone-to-implant contact ratio compared to rod sample 1 (*$P<0.005$).

The above-described in vivo animal test results suggest that the biodegradable stent according to one embodiment of the present invention can effectively improve the initial corrosion of magnesium in vivo, thus improving the in vivo stability and biocompatibility of magnesium biomaterials.

Although embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A stent comprising:
a magnesium-dominant metallic layer;
a ceramic layer formed over the magnesium-dominant metallic layer; and
a magnesium-containing non-metallic layer comprising $MgF_2$ and interposed between the metallic layer and the ceramic layer.

2. The stent of claim 1, wherein the stent comprises a wired structure, which has a cross-section comprising a core formed of the magnesium-dominant metallic layer, the non-metallic layer surrounding the core, the ceramic layer surrounding the non-metallic layer.

3. The stent of claim 1, wherein the magnesium-dominant metallic layer comprises magnesium in an amount of about 90 wt % or more.

4. The stent of claim 3, wherein the magnesium-dominant metallic layer additionally contains one or more elements selected from the group consisting of zinc (Zn), manganese (Mn), calcium (Ca), zirconium (Zr), yttrium (Y), molybdenum (Mo), niobium (Nb), tantalum (Ta), titanium (Ti), strontium (Sr), chromium (Cr), silicon (Si), phosphorus (P), nickel (Ni) and iron (Fe).

5. The stent of claim 1, wherein the non-metallic layer has a thickness of about 0.05 µm to about 1.5 µm.

6. The stent of claim 1, wherein the ceramic layer comprises at least one of hydroxyapatite (HA) and titanium dioxide ($TiO_2$).

7. The stent of claim 1, wherein the ceramic layer has a thickness of about 0.1 µm to about 10 µm.

8. A method of making the stent of claim 1, the method comprising:
providing a structure comprising the magnesium-dominant metallic layer and the magnesium-containing non-metallic layer comprising $MgF_2$ over the metallic layer; and
forming the ceramic layer over the structure such that the non-metallic layer is interposed between the metallic layer and the ceramic layer.

9. The method of claim 8, wherein providing the structure comprises:
providing the magnesium-dominant metallic layer; and
sputtering a magnesium-containing compound to provide the magnesium-containing non-metallic layer comprising $MgF_2$ over the metallic layer.

10. The method of claim 8, wherein providing the structure comprises:
providing a magnesium-dominant metallic material; and
converting magnesium in surfaces of the magnesium-dominant metallic material to a magnesium-containing compound such that the magnesium-containing compound surrounds the magnesium-dominant metallic material.

11. The method of claim 10, wherein the magnesium-containing non-metallic layer comprises magnesium fluoride ($MgF_2$).

12. The method of claim 11, wherein the magnesium fluoride ($MgF_2$) is formed by fluorination of the magnesium-dominant metallic material on surfaces thereof.

13. The method of claim 10, additionally comprising, subsequent to converting, subjecting the structure to a temperature from about 200° C. to about 500° C.

14. The method of claim 8, wherein the ceramic layer is formed by vacuum powder spraying of a ceramic material over the magnesium-containing non-metallic layer.

15. The method of claim 8, wherein the ceramic layer is formed by applying a hydroxyapatite powder or titanium dioxide powder having a particle size of about 1 to about 5 μm over the magnesium-containing non-metallic layer.

16. A method of making the stent of claim 1, the method comprising:
 providing a magnesium-dominant metallic material in a stent shape;
 forming the magnesium-containing non-metallic layer comprising $MgF_2$ over the magnesium-dominant metallic material; and forming the ceramic layer over the magnesium-containing compound layer.

17. The method of claim 16, wherein forming the magnesium-containing compound non-metallic layer comprises processing the magnesium-dominant metallic material to convert a portion of magnesium of the magnesium-dominant metallic material into a magnesium-containing compound thereby forming the magnesium-containing non-metallic layer that surrounds the magnesium-dominant metallic material.

18. The method of claim 16, wherein forming the magnesium-containing non-metallic layer comprises sputtering a magnesium-containing compound onto a surface of the magnesium-dominant metallic material.

* * * * *

UNITED STATES PATENT AND TRADEMARK OFFICE
CERTIFICATE OF CORRECTION

PATENT NO. : 8,382,823 B2   Page 1 of 1
APPLICATION NO. : 12/765715
DATED : February 26, 2013
INVENTOR(S) : Kim et al.

It is certified that error appears in the above-identified patent and that said Letters Patent is hereby corrected as shown below:

On the Title Page Item [73]:
"SNU R&DB Foundation, Seoul (KR)" should read, --SNU R&DB Foundation, Seoul (KR); Iljin Copper Foil Co., LTD., Jeollabuk-do (KR)--.

Signed and Sealed this
Eighth Day of April, 2014

Michelle K. Lee
*Deputy Director of the United States Patent and Trademark Office*